United States Patent [19]

Moriya et al.

[11] Patent Number: 5,298,963
[45] Date of Patent: Mar. 29, 1994

[54] APPARATUS FOR INSPECTING THE SURFACE OF MATERIALS

[75] Inventors: Kazuo Moriya; Takayuki Tsuzura, both of Ageo, Japan

[73] Assignee: Mitsui Mining & Smelting Co., Ltd., Tokyo, Japan

[21] Appl. No.: 842,073

[22] Filed: Feb. 26, 1992

[51] Int. Cl.$^5$ .......................................... G01N 21/88
[52] U.S. Cl. .................................... 356/31; 356/237; 356/371
[58] Field of Search .................. 356/30, 31, 237, 371, 356/23

[56] References Cited

U.S. PATENT DOCUMENTS

| | | | |
|---|---|---|---|
| 3,782,836 | 1/1974 | Fey et al. | 356/30 |
| 3,835,247 | 9/1974 | Soames | 250/205 |
| 4,449,818 | 5/1984 | Yamaguchi et al. | 356/371 |
| 4,720,191 | 1/1988 | Siegel et al. | 356/237 |
| 4,882,498 | 11/1989 | Cochran et al. | |
| 4,896,211 | 1/1990 | Hunt et al. | |
| 4,908,517 | 3/1990 | Imamura | |
| 4,925,298 | 5/1990 | Dobrilla | |
| 4,933,567 | 6/1990 | Silva et al. | |
| 4,952,058 | 8/1990 | Noguchi et al. | |
| 4,958,373 | 9/1990 | Usami et al. | 356/237 |
| 4,992,949 | 2/1991 | Arden | 356/237 |

OTHER PUBLICATIONS

Flamholz et al. "Scratch and Line Defect Detection System Using Oblique Light Modified to Detect Preferentially Scattered Light" *IBM Technical Disclosure Bulletin*, vol. 20, No. 1 (Jun. 1977) pp. 170–173.

Grosewald et al. "Automatic Detections of Defects on Wafers" *IBM Technical Disclosure Bulletin*, vol. 21, No. 6 (Nov. 1978) pp. 2336–2337.

*Primary Examiner*—Richard A. Rosenberger
*Attorney, Agent, or Firm*—Bucknam and Archer

[57] ABSTRACT

An apparatus for inspecting the surface of a sheet-like object has a movable stage with an object mounted thereon; a source for lighting the object on the stage, particularly by making a plurality of illumination lights respectively having different wavelengths incident on the surface of the object from respective predetermined directions; image pickup device for fetching the image of the object under illumination of the light as image data or the images of parts of the object as image data obtained on the respective different wavelengths; image data processing device for inspecting the image data for defects; and a device for synchronizing control either for flashing the light at a predetermined time interval just after the stage commences its movement, synchronously with fetching the image data or for flashing the light and simultaneously fetching the image data obtained on the respective different wavelengths, synchronously with the object on the stage reaching respective predetermined positions while moving the stage.

9 Claims, 16 Drawing Sheets

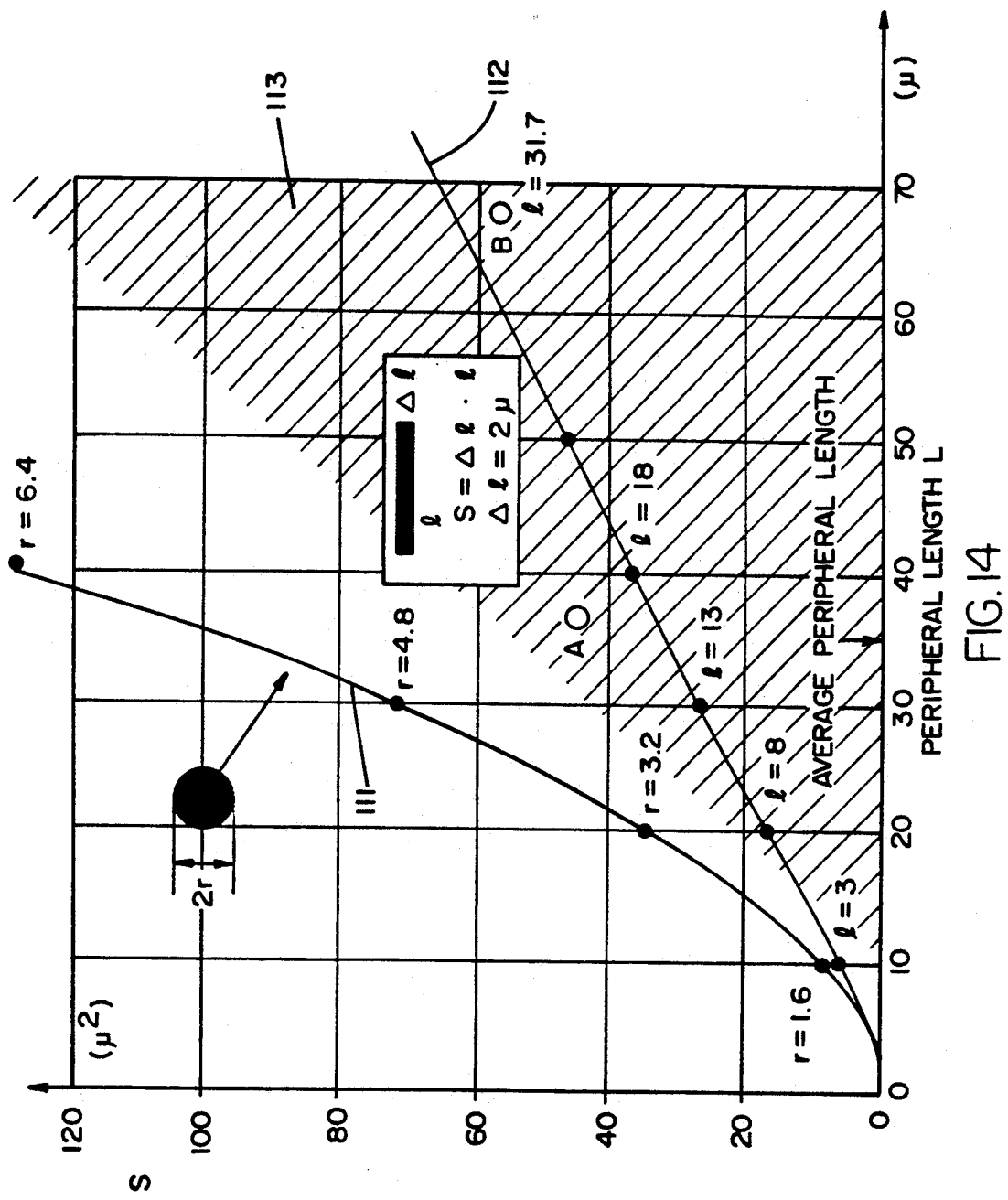

APPARATUS FOR INSPECTING THE SURFACE OF MATERIALS

BACKGROUND OF THE INVENTION

1. Field of the Invention

This invention relates to an apparatus for inspecting the surface of materials, which enables to rapidly and surely measure and estimate materials such as crystalline materials for their surface defects.

2. Prior Art

There have heretofore been known apparatus for measuring and observing materials, such as crystalline materials e.g. semiconductor wafers, to know the surface defects and the like of said materials. For example, Japanese Pat. Appln. Laid-Open Gazette No. Sho 60-101942 (No. 101942/1985) discloses an apparatus for measuring and observing defects such as etch pits (recesses or grooves caused by the defects of crystals) produced by subjecting a wafer-like sample (an object to be inspected) to etching or other treatments.

The structure of a conventional apparatus for measuring and observing such defects of crystalline materials as the above is roughly shown in FIG. 19 of the accompanying drawings.

In FIG. 19, numeral 1 indicates a wafer sample which has been subjected to etching, as an object to be examined for measurement and estimation, and numeral 2 a stage on which the wafer sample 1 is mounted. This stage 2 is constructed so that it can be moved in the longitudinal direction (X direction which is vertical to the surface of paper having said FIG. drawn thereon), in the lateral direction (Y direction which is the left- and right-side direction in said FIG.) and in the height direction which is the upper-and-lower direction in said FIG. To allow the stage 2 to be movable in these directions, the stage 2 is provided with drive mechanisms 2b, 2c and 2d each having a pulse motor (stepping motor) and the like. Numeral 3 indicates a pulse motor controller which sends a drive signal to each of the pulse motors of the mechanisms 2b, 2c and 2d in the directions X, Y and Z; and numeral 13, a pulse motor driver which outputs pulse signals to the pulse motors according to drive signals outputted from the pulse motor controller 3.

Numeral 4 indicates a microscope for observing and measuring the wafer sample 1 mounted on the stage 2. This microscope 4 is fitted with an illumination lamp (halogen lamp) 5 which is a light source for lighting up the sample 1, and with a TV camera 6 for photographing a stationary image of the sample 1. Numeral 14 indicates a microscope control unit for controlling an autofocus mechanism of the microscope 4.

Numeral 7 indicates an image processing unit for estimating defects of the sample 1, such as etch pits, on the basis of image data inputted by the TV camera 6; numeral 8, a computer for controlling communication between the pulse motor controller 3 and the image processing unit 7, and for manipulation of data obtained from the image processing unit; and numeral 9, a monitor for displaying image data obtained from the image processing unit 7.

With the conventional apparatus having such a structure as above, the surfaces of samples are inspected as follows.

First of all, the sample 1 is set on the stage 2. The computer 8 gives instructions to the pulse motor controller 3 to move and stop the stage 2 at a predetermined position. Then, there is procured an enlarged image of the sample 1 obtained through the microscope 4 under the lighting lamp 5. The enlarged image so procured is inputted, as image data, through the TV camera 6 to the image processing unit 7. Thereafter, the image data is subjected to image processing at the image processing unit 7 and the computer 8 to measure (calculate) and estimate the distribution, number, shape, density and the like of defects or imperfections contained in or on crystals.

After the end of the above processes or treatments, the stage 2 with the sample 1 mounted thereon is moved to the next position for measurement whereupon the sample 1 in the stationary state is subjected to the same processes as above thereby to measure and evaluate the defects of the wafer sample.

FIG. 20A shows how the entire surface of the wafer sample 1 is inspected. In this Fig., each of rectangles 41 indicates a unit area for observation, this observation unit area enabling a magnified image thereof to be obtained through the microscope, in other words, an observation unit area enabling image data thereof to be fetched at one time (for example, an observation unit area such as 0.5 mm×0.5 or 1 mm×1 mm). The stage 2 is so moved as to make a measurement of each rectangle 41 one by one in the order indicated by an arrow mark 42 so as to measure the entire surface of the wafer sample 1 for defects.

FIG. 20B shows how the predetermined unit areas of the wafer sample 1 are measured. Each of rectangles 43 indicates an observation unit area which enables a magnified image thereof to be obtained through the same microscope 4 as used for the rectangles 41 in FIG. 20A. The stage 2 is so moved as to measure the rectangular areas 43, which are observation unit areas, one by one so as to measure these unit areas of the wafer sample 1 for their defects.

In the aforementioned conventional apparatuses for inspecting the surface of materials, the stage 2 is once stopped when image data is obtained and the thus obtained image data is processed during the stoppage of the stage 2 so that it is impossible to increase the average moving speed of the stage. In addition, movement of the stage and processing of the image data are not carried out simultaneously, but they are done respectively at different times. Accordingly, it takes a long time for one sample to be measured and, therefore, this decreases the capability of measurement of the apparatuses and processing particularly when measurement is made on the entire surface of a wafer sample as shown in FIG. 20A. For example, in the case where the entire surface of a semiconductor having a 6-inch diameter was measured using a conventional commercially available apparatus, the time needed for the measurement was about 10 hours.

Further, in cases where a wafer sample to be inspected has foreign matters, such as dust, attached thereto and the wafer sample has flows on the surface, it is difficult to distinguish these dust and flaws from the etch pits to be inspected. Even if the image processing unit 7 and computer 8 were used to try to distinguish etch pits from other things, sufficient distinction therebetween would be impossible.

SUMMARY OF THE INVENTION

One object of this invention is to provide, in view of the above disadvantages, a surface inspecting apparatus which enables the moving speed of a stage to be increased, enables the inputting of images without stopping the movement of the stage, allows the necessary image inputting to be carried out extremely simply and appropriately and enables a more rapid inspection of surfaces of materials than conventional apparatus.

Another object is to provide a surface inspecting apparatus which is capable of distinguishing etch pits from other items correctly and precisely even in cases where an object to be inspected has thereon flaws and/or foreign matters such as dust.

In one aspect of this invention, a surface inspecting apparatus for measuring and estimating the surface of a planar (or sheet-like) object to be inspected, comprises:
a movable stage with a to-be-inspected object mounted thereon,
lighting means for lighting the object mounted on the stage,
image pickup means for fetching parts of the object as image data,
image processing means for estimating defects of the object on the basis of the image data, and
synchronization control means for flashing the lighting means synchronously with the object mounted on the stage reaching predetermined positions during the movement of the stage, so as to fetch the image data by the image pickup means.

In substitution for flashing of the lighting means simultaneously with the image data being fetched, the lighting means may be flashed simultaneously with the image data being fetched at a predetermined time interval just after the start of movement of the stage.

In a second aspect of this invention, a surface inspecting apparatus for measuring and estimating the surface of a sheet-like object, comprises:
lighting means for marking a plurality of illumination lights respectively having different wavelengths incident on the surface of the object from respective predetermined different directions to light up the surface of the object,
image pickup means for fetching the object images respectively generated by the illumination lights having different wavelengths, as the image data obtained on the respective different wavelengths, and
image processing means for measuring and estimating the defects of the object on the basis of said image data obtained on the respective different wavelengths.

In a third aspect of this invention, a surface inspecting apparatus for measuring and estimating the surface of a sheet-like object, comprises:
a movable stage with the object mounted thereon,
lighting means for making a plurality of illumination lights, respectively having different wavelengths incident on the surface of the object from respective predetermined different directions to light up the surface of the object,
image pickup means for fetching the images of parts of the object, the images being respectively generated by the illumination lights having different wavelengths, as the image data obtained on the respective different wavelengths,
image processing means for measuring and estimating the defects of the object on the basis of said image data obtained on the respective different wavelengths, and
synchronization control means for flashing the lighting means synchronously with the object mounted on the stage reaching predetermined positions during the movement of the stage, thereby to fetch the image data obtained on the respective wavelengths by said image pickup means.

In substitution for the fact that flashing of the lighting means and fetching of the image data are carried out synchronously with the position of the object as mentioned above, the lighting means may be flashed to fetch the image data at a predetermined time interval just after the start of movement of the stage.

In the image processing means, for example, image data obtained on the respective different wavelengths is subjected to the computation of exclusive-or (EX-OR) so as to evaluate or estimate the defects of the object.

The stage is preferably provided with a stage plate for mounting the object thereon and drive mechanisms for rapidly moving the stage plate. The lighting means uses, for example, a strobe-light. Said image pickup means is preferably provided with a microscope having an autofocus mechanism and an image pickup element fixed to said microscope.

According to this invention, either when a to-be-inspected object, such as a wafer material, reaches predetermined positions while moving it at a high speed, or at a predetermined time interval, a lighting means is flashed and, at the same time, image data can be fetched as a stationary image by an image pickup means. The image data may be subjected to image processing so as to measure and estimate defects of the wafer material automatically and highly efficiently.

In a case where a plurality of illumination lights respectively having different wavelengths are made incident on a to-be-inspected object from respective predetermined different directions to obtain image data on the respective wavelengths and estimate the defects of the object on the basis of the image data so obtained, almost all measurement errors which would otherwise be made due to dust, flaws and the like on the object, can be avoided.

BRIEF DESCRIPTION OF THE DRAWINGS

FIG. 14 is a graph which expresses peripheral length versus area in terms of a circular image and a rectangular image;

DESCRIPTION OF THE PREFERRED EMBODIMENTS

Figure 1:
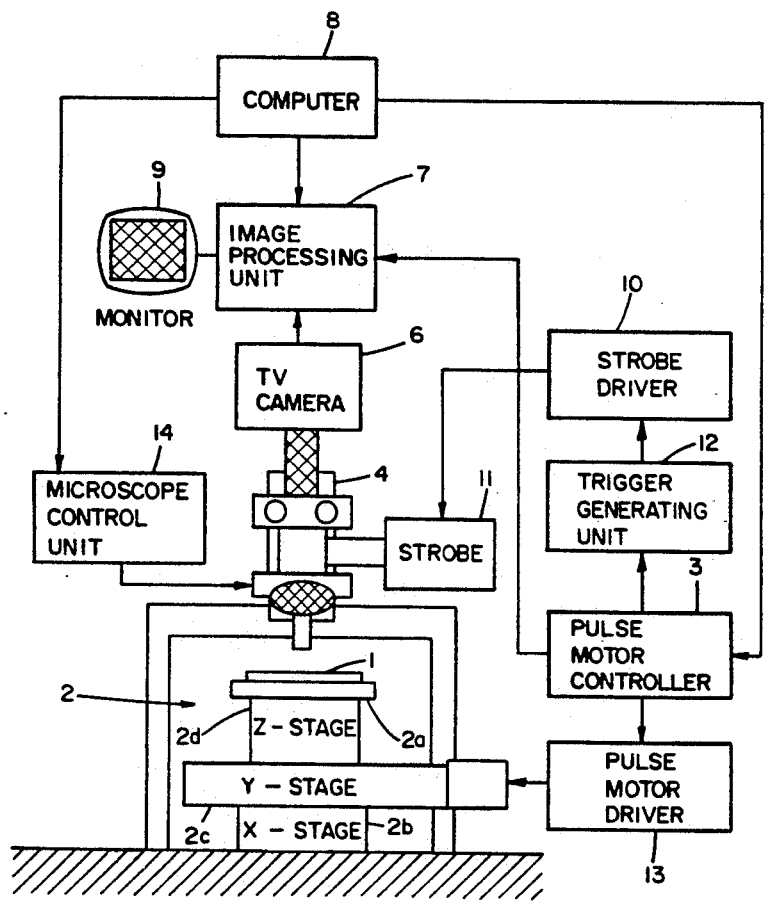
FIG. 1 is a block diagram roughly showing the structure of a first embodiment of an apparatus for the inspection of the surface of a material according to this invention.

This invention will be hereunder explained in detail with reference to Embodiments of Examples indicated in the drawings.

Figure 19:
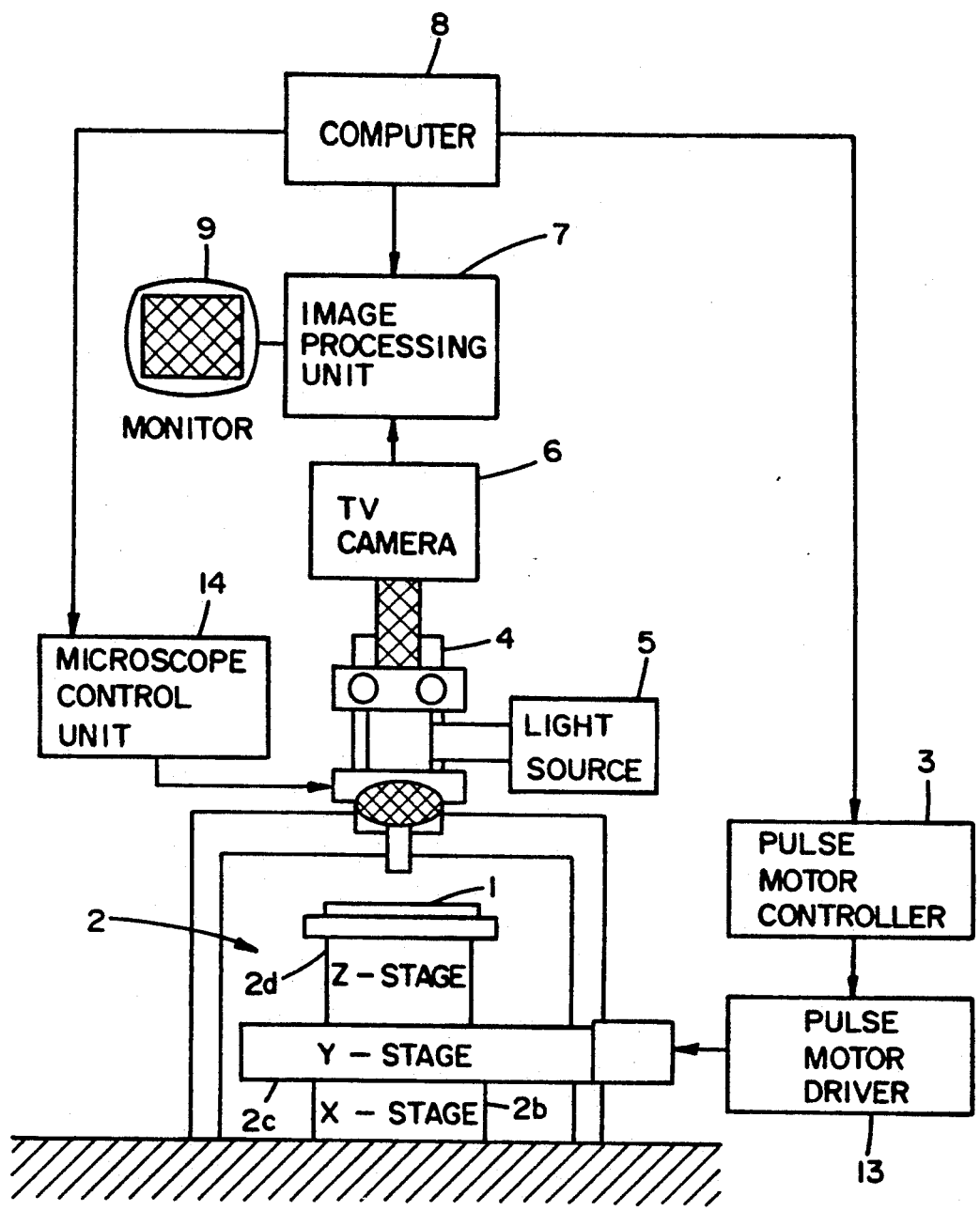
FIG. 19 is a block diagram roughly showing the structure of a conventional apparatus for inspecting the defects of a material.

FIG. 1 is a view roughly showing the structure of a first embodiment of an apparatus for inspecting the surface of a material for defects. In this FIG., the same parts or equivalents thereto as those in the previously mentioned FIG. 19 are given the same numerals, respectively, for the sake of simplicity.

In FIG. 1, 2a is a sample stage provided with a vacuum chuck for fixing a wafer; 2b, 2c and 2d indicate electric motor drive mechanisms provided with pulse motors for driving in the X, Y and Z directions, respectively. A sample stage 2a houses therein a rotation drive mechanism (not shown) for rotating in the θ direction (the direction of rotation around the z direction as the rotation axis). The stage can be moved in the X (longitudinal), Y (lateral), Z (height) and θ (rotation) directions at a high speed. The stage 2 can be precisely moved so that every part of the surface of the wafer sample 1 is brought into the visual field of the microscope 4 by the use of the stage drive mechanisms 2a, 2b, 2c and 2d, a pulse motor driver 13 and a pulse motor controller 3.

The microscope 4 is fitted with a TV camera 6, a strobe light 11 and a microscope control unit 14 for controlling the autofocus mechanism of the microscope 4.

Figure 2:
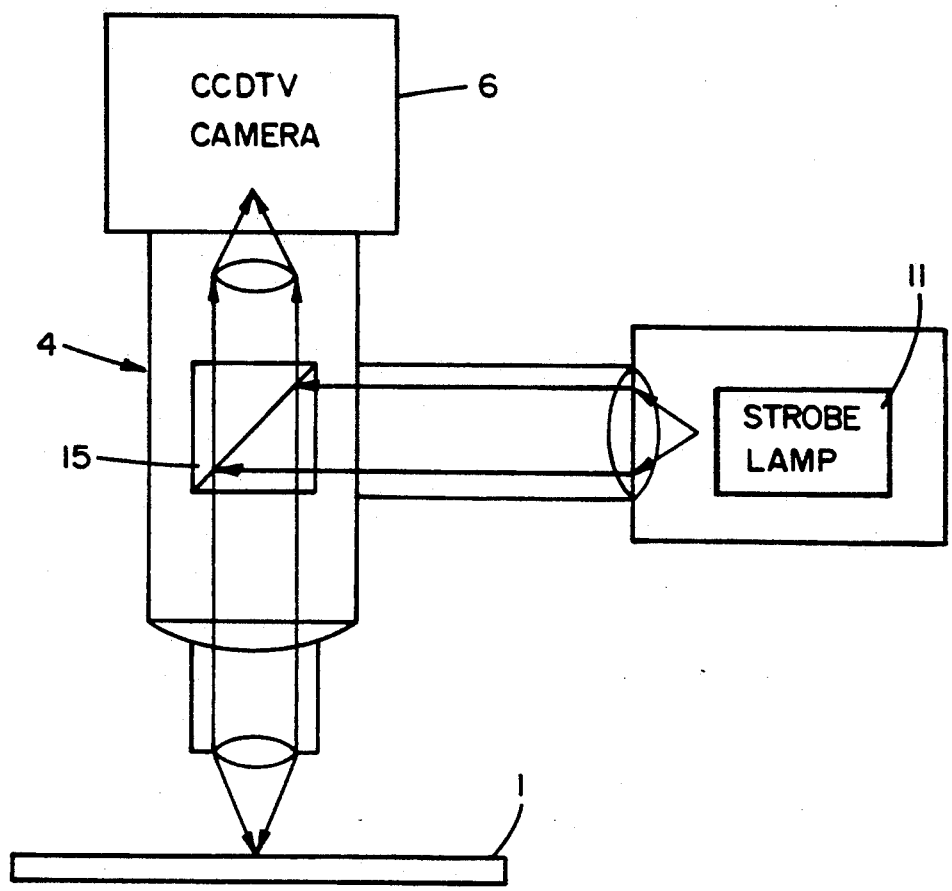
FIG. 2 is a rough sectional view showing the strobe light, microscope, TV camera and the like of the apparatus of FIG. 1.

FIG. 2 is a sectional view roughly showing the strobe light 11, microscope 4, TV camera 6, etc. Numeral 15 indicates a half mirror. The light irradiated from the strobe light 11 is reflected by the half mirror 15 and is then irradiated through the optical system of the microscope 4 to the wafer sample 1 which is an object to be inspected. The light from the wafer sample 1 is made incident on the TV camera 6 through the half mirror 15.

Referring again to FIG. 1, a trigger generating unit designated at 12 produces strobe lighting and a trigger signal for fetching images on the basis of signals outputted from the pulse motor controller 3. The trigger signal for strobe lighting is outputted to a strobe driver 10 which then flashes the strobe light in response to the trigger signal so outputted. The trigger signal for fetching images is outputted to an image processing unit 7 and, in response to this, the image processing unit 7 fetches image data from the TV camera 6. Accordingly, it follows that instantaneous microscopic images of the surface of the wafer sample 1 which are obtained during the high speed movement thereof, are fetched as stationary images synchronously with strobe flash timing. On the basis of this image data, the image processing unit 7 in cooperation with a computer 8, makes a measurement and estimation of the sample 1 for its defects.

Using the apparatus having such a structure as above, the inspection of the surface of the sample 1 is carried out as follows.

Figure 20A:
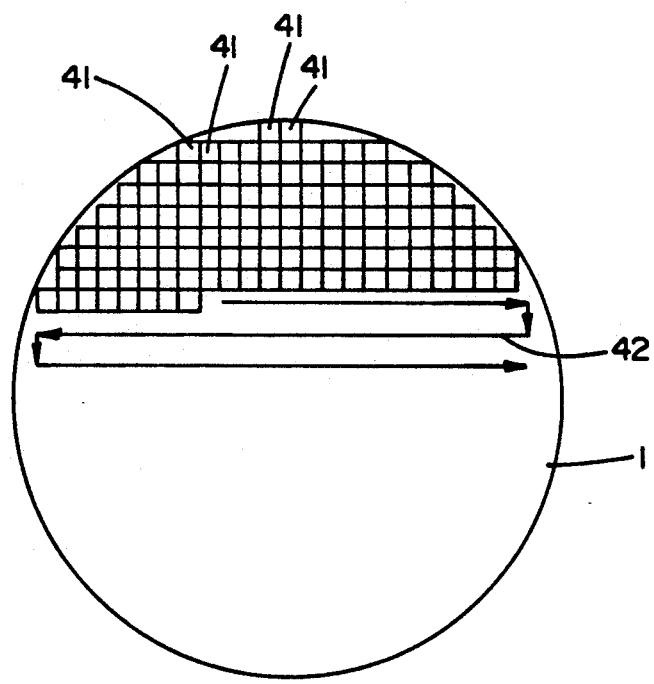
FIGS. 20A and 20B are each plan views showing how to measure a wafer which is a to-be-inspected object, for defects.
Figure 20B:
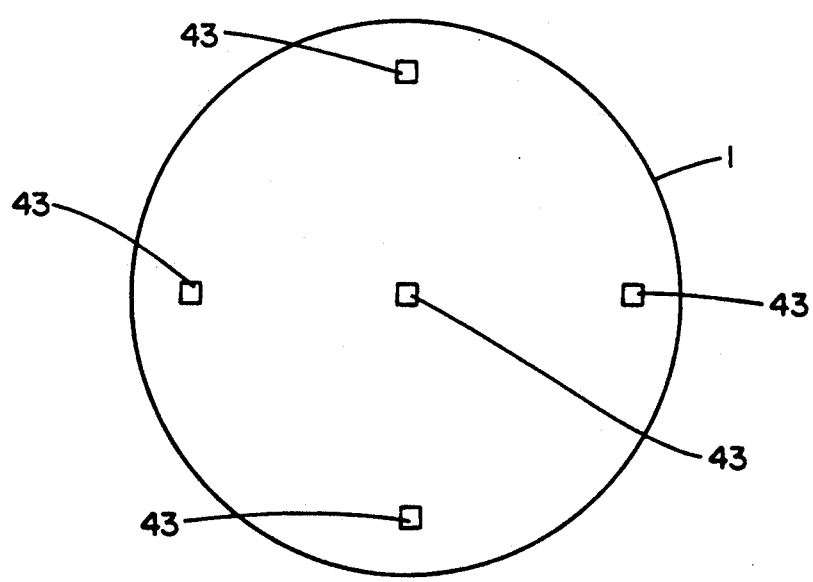

First of all, the sample 1 is set on the stage 2. The computer 8 instructs the pulse motor controller 3 to output a predetermined pulse signal. Based on the instructions from the computer 8, the pulse motor controller 3 outputs a pulse signal to each pulse motor of the stage 2 so that the stage 2 is continuously moved at a high speed in a predetermined direction (for example, so that the rectangular regions 41 which are each an area to be inspected, are inspected one by one in the order indicated by arrow marks 42 as shown in FIG. 20A). In this manner, the stage 2 is continuously (not stepwise) moved.

The trigger generating unit 12 produces strobe flashing and trigger signals for fetching images, based on pulse signals outputted from the pulse motor controller 3. Precisely speaking, pulse signals for driving the motors (or for driving the stage) are outputted from the pulse motor (stepping motor) controller 3, and the pulse signals so outputted are then divided or demultiplied thereby to produce trigger signals. The stepping motor proceeds one step every one pulse signal inputted. Assuming that the stage proceeds 1 μm every one pulse signal inputted and that a signal obtained by dividing the pulse signal by 1000 is a trigger, a trigger signal is outputted from the trigger generating unit 12 every time the stage 2 proceeds 1 mm (1000 μm). In response to this trigger signal, the strobe driver 10 flashes the strobe light 11 and the image processing unit 7 fetches image data. In this case, regardless of the moving speed of the stage 2, the fetching of image data is carried out according to a distance over which the stage 2 is moved (that is, the position of the stage 2).

The fetching of image data by the image processing unit 7 is achieved by, first of all, obtaining a magnified image of the sample 1 through the microscope 4 under flashing of the strobe 11 and the magnified image is inputted as the image data through the TV camera 6 to the image processing unit 7. Then, the image data is subjected to image processing in the image processing unit 7 and the computer 8 so as to measure (compute) the distribution, number, shape and density of crystal defects.

The above treatments are continuously effected while moving the sample 1. For example, as the rectangular regions (unit areas to be observed) 41 are observed in the order indicated by arrow marks 42 in FIG. 20A, the sample 1 is subjected to the above measurements while continuously moving the sample 1. In this manner, the wafer sample 1 is measured for its defects.

The image processing unit fetches image data under the flashing of the strobe while the stage is continuously moved without stoppage of the movement, and image processing (measurement) of the image data is effected during the movement of the stage. Since the present image processing is carried out without repetition of movement and stoppage unlike conventional image processing, the former can naturally be carried out at a higher speed. The moving speed of the stage can thus be raised to the processing speed of the image processing and, therefore, the overall processing speed comes to depend approximately on the image processing speed. If it were attempted to increase the processing speed of the conventional measurement, a stage would have to repeat rapid acceleration and rapid stoppage with the result that an apparatus for the measurement would be large-sized and complicated. In addition, it is also pointed out that a strobe could not be used in the conventional apparatus and image data stage because in this case the images would run (or become like a blurred photograph) and could not be measured for defects.

The measurement of each image by said conventional apparatus needed 1-2 seconds, whilst that of each image by said present apparatus in the Examples needed 1/10-2/10 seconds.

Figure 3:
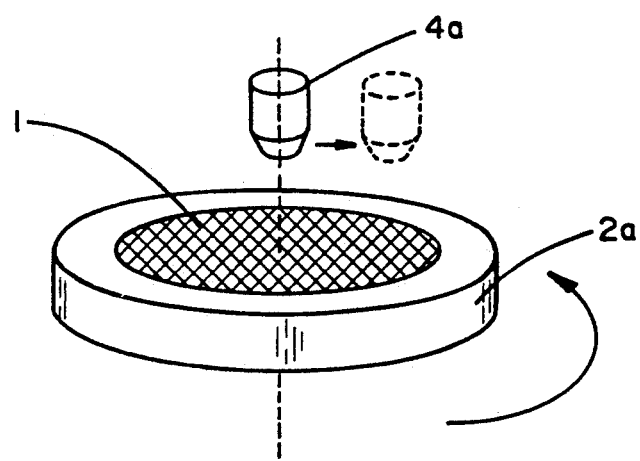
FIG. 3 is a perspective view illustrating the operations of a sample stage and microscope.

Further, the movement of the sample stage 2 having the wafer sample 1 mounted thereon is controlled in the directions of three axes of X, Y and Z; to investigate the distribution of crystal defects, however, other various modifications of control are available without being limited to the above three-axial control (surface scanning). For example, as indicated in FIG. 3, an object lens 4a of the microscope 4 may be moved from the central portion of the wafer 1 to the lateral or longitudinal direction thereof while rotating the sample stage 2, thereby to fetch images in order to measure and estimate the wafer 1 for its crystal defects. In this case, while rotating the stage at a fixed high velocity and stepwise moving the object lens laterally by the distances each equal to the width of the visual field of the object lens, images are sampling-fetched by a strobe at the respective positions every one rotation. The images so fetched become ones which appear to have collected ring-like data.

In the drive system for the stage 2 of the Example of this invention, a pulse motor is used; however, various other drive systems such as a servomotor and an ultrasonic motor may be used without being limited to such a pulse motor.

Further, the trigger generating unit 12 having a function of producing timing signals may be substituted by the computer 8, and such trigger signals may be produced by the computer 8. The trigger generating unit may be housed in the stage drive controller 3 or the drive circuit portion 10 of the strobe 11. The stage portion (motor portion) may be fitted with an encoder (sensor) to produce trigger signals from the signals of the encoder.

Trigger signals are outputted in response to the positional information outputted from the pulse motor controller 3, or otherwise image data may be fetched at a predetermined interval starting at the time of commencement of the measurement for making the measurement.

Further, although a description of image input with the use of a strobe has so far been made herein, a mechanism capable of exerting the same effect as above without the use of a strobe may be provided instead. In solid image pickup cameras such as CCD (charge-coupled device) for example, quite the same effect may also be obtained by using a shutter camera in which the image pickup element has an electric shutter function or by using a TV camera in which a high-speed shutter is provided in front of the image pickup element.

Then, referring to FIGS. 4-18, a second embodiment of this invention will be explained hereunder.

Figure 4:
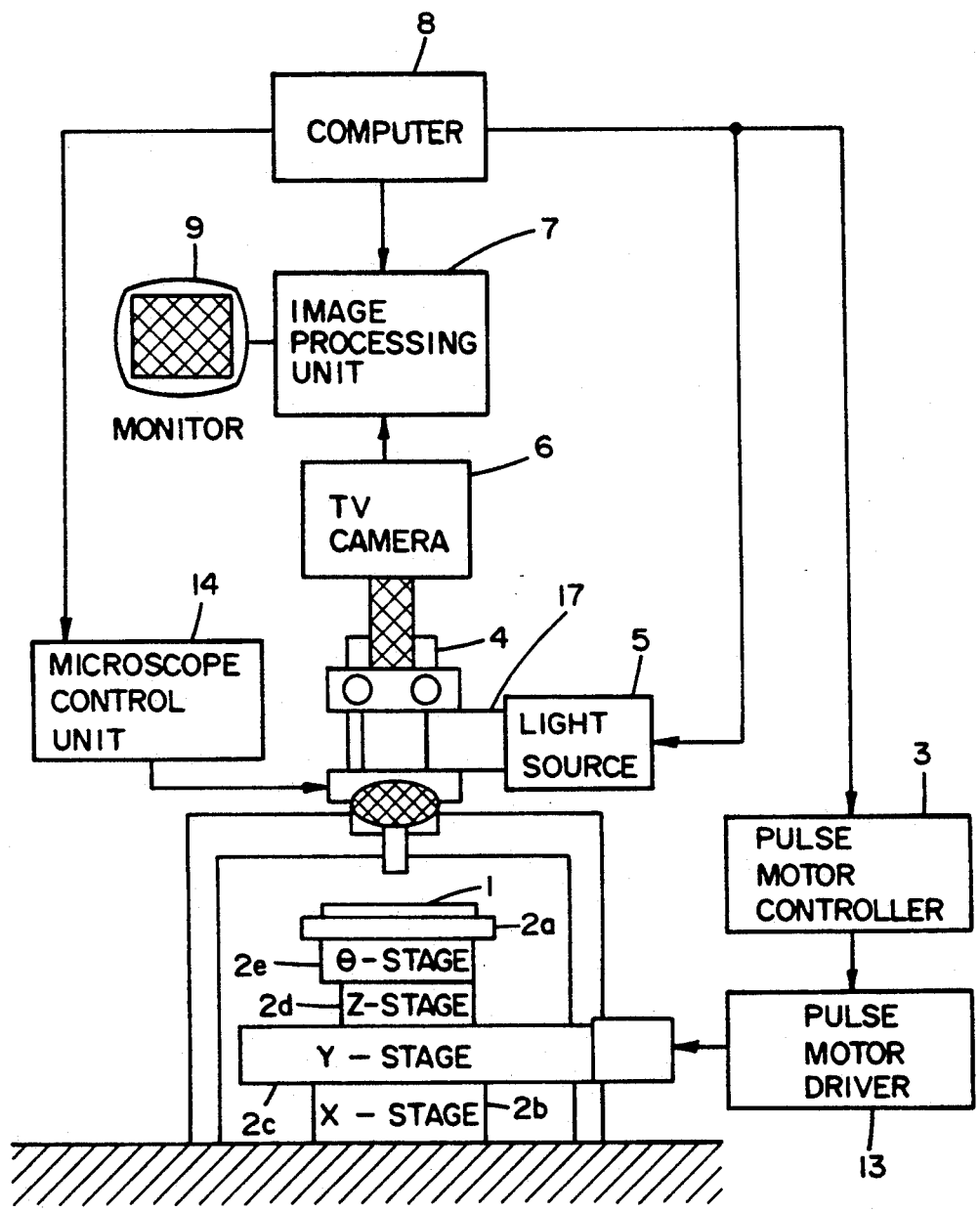
FIG. 4 is a block diagram roughly showing the structure of a second embodiment of an apparatus for the inspection of the surface of a material according to this invention.

FIG. 4 shows a rough structure of a second embodiment (Example) of an apparatus for inspecting the surface of a material according to this invention. In this Figure, the same parts or equivalents thereto as those in FIG. 19 are given the same numerals as those in FIG. 19, respectively, for the sake of simplicity.

In FIG. 4, 2a is a sample stage fitted with a vacuum chuck for fixing a wafer; and 2e, a $\theta$ stage drive mechanism for rotating the sample stage 2a in the $\theta$ direction (the direction of rotation around the Z direction). The $\theta$ stage drive mechanism 2e is positioned above electromotive stage drive mechanisms 2b, 2c and 2d for moving the stage in the respective directions of X, Y and Z. The stage 2 can be moved so precisely as to include any parts of the wafer 1 in the visual field of the microscope 4 by the use of the stage drive mechanisms 2b, 2c and 2d, the pulse motor driver 13 and the pulse motor controller 3. Further, the direction of illumination of an illumination light and that of defects can be coincided with each other by changing an angle at which the sample 1 is rotated, as stated below.

The microscope 4 is provided with an optical system 17 for irradiating monochromatic lights respectively having different wavelengths from specified directions. The light source 5 is an ordinary halogen lamp, but it enables such monochromatic lights respectively having different wavelengths as above to be irradiated from specified directions with aid of color filters of the optical system 17 and dark visual field illumination (which will be explained later in more detail). The TV camera 6 is a color TV camera and can fetch images obtained from the respective different wavelengths of the monochromatic illumination lights. Image data of microscopic images obtained by the use of the above illumination and the TV camera 6 are inputted to the image processing unit 7 whereupon the processing unit 7 and the computer 8 measure and estimate the wafer sample 1 for its surface defects.

Prior to explaining the operation of an apparatus of FIG. 4 in detail, there will be explained etch pits which are formed as defects on the surface of a wafer.

Many of the etch pits appearing on the surface of a wafer only have one specified surface. For example etch pits, which are stacking faults, on the surface (100) of a silicon (Si) wafer are long in the direction parallel to the surface (110) and are formed of a surface which makes an angle of about 11° with the surface (100).

Figure 5:
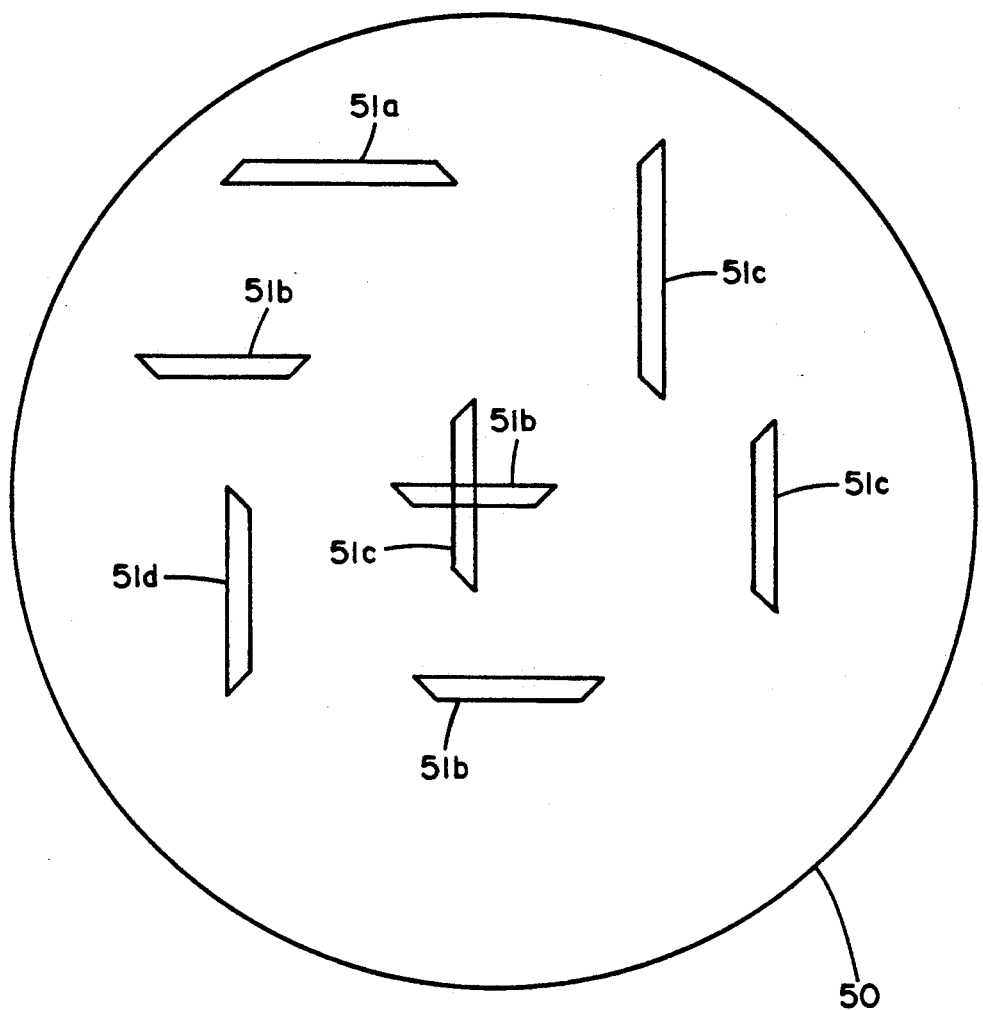
FIG. 5 is a view showing oxygen induced stacking faults (OSF) on the surface of a Si wafer.
Figure 6:
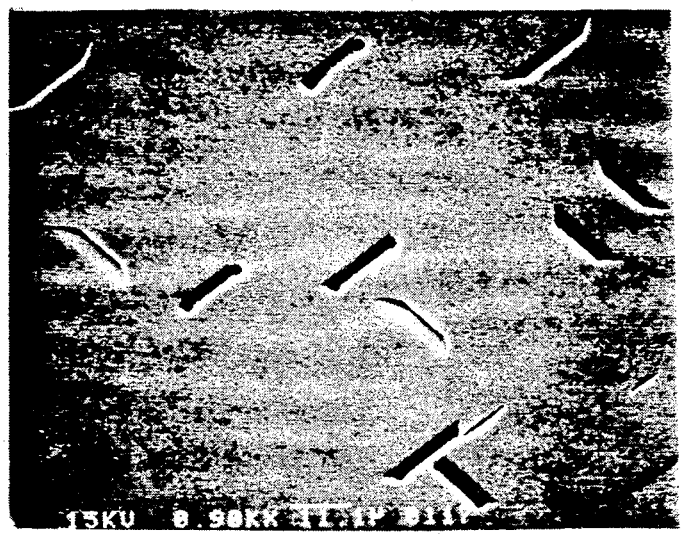
FIG. 6 is a scanning electron microscope (SEM) photograph showing the crystalline structure of OSF etch pits on the surface of a Si wafer.
Figure 7:
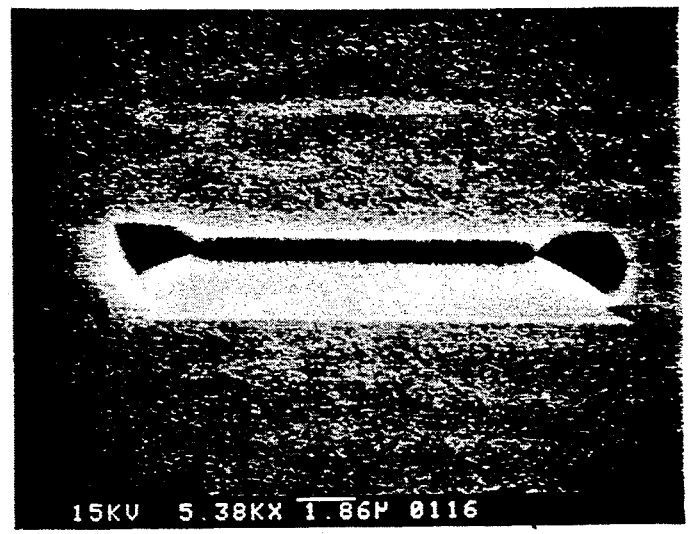
FIG. 7 is a scanning electron microscope photograph showing the crystalline structure of one etch pit.
Figure 8:
FIG. 8 is a sectional view taken along the L-L' line of FIG. 7.

FIG. 5 shows oxidation induced stacking faults (OSF) on the surface of a Si wafer. FIG. 6 shows images of OSF etch pits on the surface of a Si wafer, the images being obtained by a scanning electron microscope (SEM); FIG. 7, the SEM image of one etch pit; and FIG. 8, a sectional view taken along the L-L' line of FIG. 7. The actual magnitude of etch pits is about 2-3 $\mu$m in width and about 10 $\mu$m or a little more in length, and FIG. 5 shows etch pits in a magnified form.

Referring to FIGS. 5-8, in the case of oxidation induced stacking faults (OSF) on the surface of a Si wafer 50, there appear only crystal surfaces directed respectively to directions 51a, 51b, 51c and 51d, as etch pits. Thus, irradiation of an illumination light in one direction enables observation of only a crystal surface directed to one direction.

Figure 9:
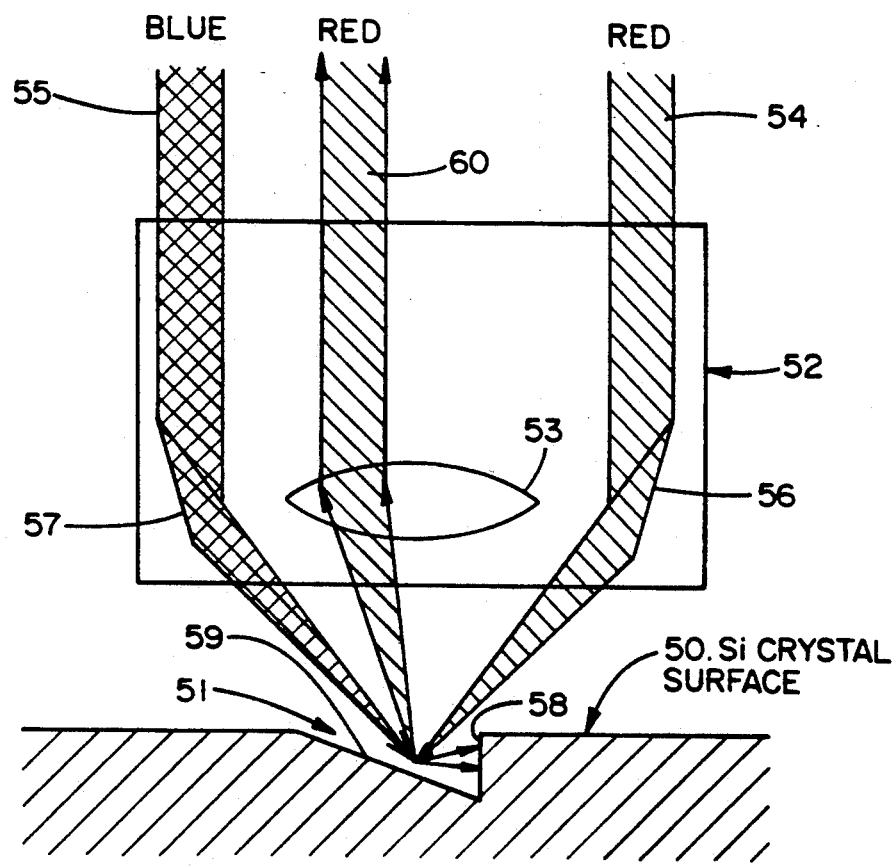
FIG. 9 is a sectional view showing that an etch pit on the surface of a Si wafer is irradiated with lights respectively having different wavelengths respectively from two different directions.

FIG. 9 is a diagrammatic view showing application of lights respectively having different waves to an etch pit 51 of a Si wafer 50 respectively from two different directions. Numeral 52 indicates an optical system including the microscope 4 (FIG. 4) and numeral 53 indicates an object lens. The optical system 52 includes, near the object lens 53, mirrors 56 and 57 for changing the light path of illumination lights.

In the apparatus of this embodiment (or this Example), light flux 54 of a red-colored illumination light and light flux 55 of a blue-colored illumination light are introduced into the optical system 52 where they are then reflected respectively at the mirrors 56 and 57. Thus, the red-colored light flux 54 and the blue-colored light flux 55 are applied to the surface of the Si wafer 50 respectively from different directions. Now suppose that the etch pit 51 is present on the position of the surface of the Si wafer 50, on which the light fluxes 54 and 55 are made incident. If so, specified crystal surfaces appear on said surface as etch pits as mentioned above. In cases where the etch pit 51 consists of surfaces 58 and 59, the blue-colored light flux 55 made incident from the left side of FIG. 9 is reflected at the surface 59 of the etch pit 51 and is then made incident on the surface 58. The blue-colored light flux 55 reflected on the surface 59 of the etch pit is blocked on the surface 58 or passes away outside of the cone of acceptance of lens 53. On the other hand, the red-colored light flux 54 made incident from the right side of said FIG. is reflected at the surface 59 of the etch pit 51 and is then made incident on the object lens 53 whereupon the light flux is detected as a red-colored reflected light 60.

Figure 10:
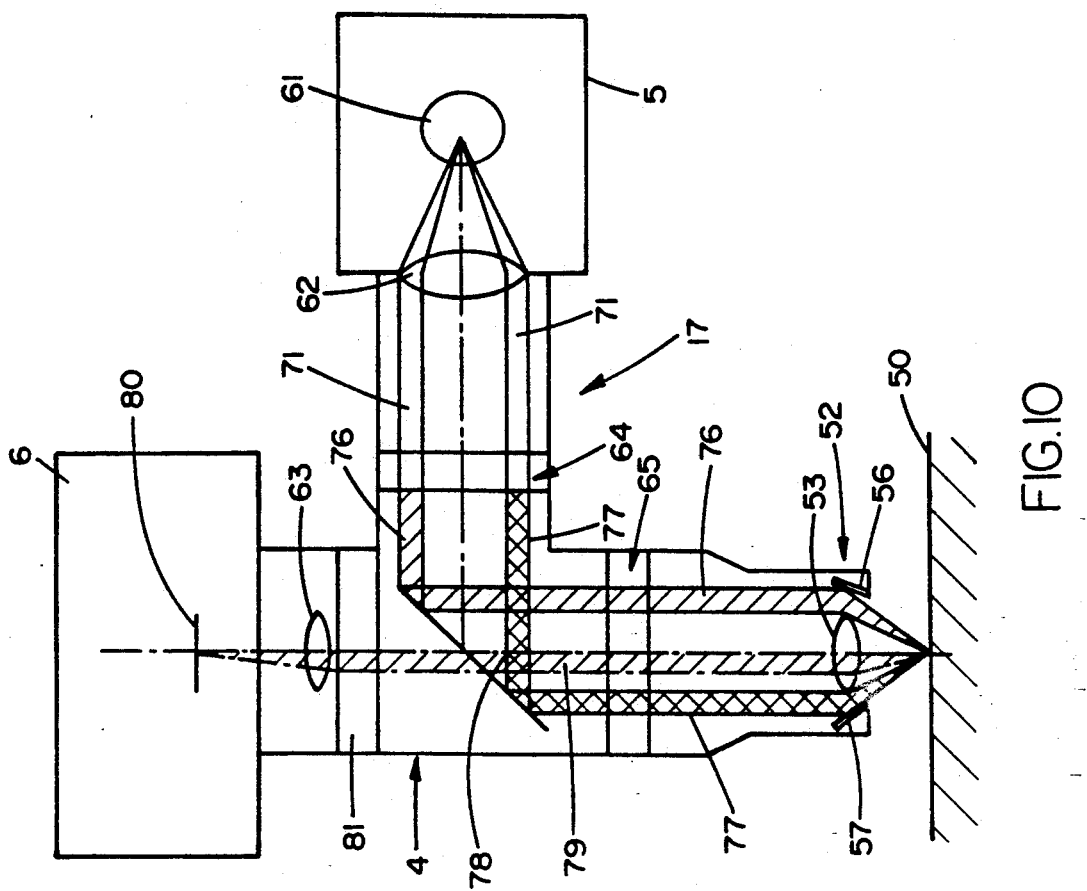
FIG. 10 is a partially sectional view showing the optical system 17 and the microscope 4.

FIG. 10 is a partially sectional view of the optical system 17 of FIG. 4 and the microscope 4. In this FIG., a light source 5 has a halogen lamp 61; the optical system 17 has a condensing lens 62 and a filter 64; and the microscope 4 has a half mirror 78, the object lens 53, the mirrors 56 and 57 for changing a light path and a condensing lens 63. In substitution for the filter 64, the same filter may be provided at a position designated at 65.

Figure 11:
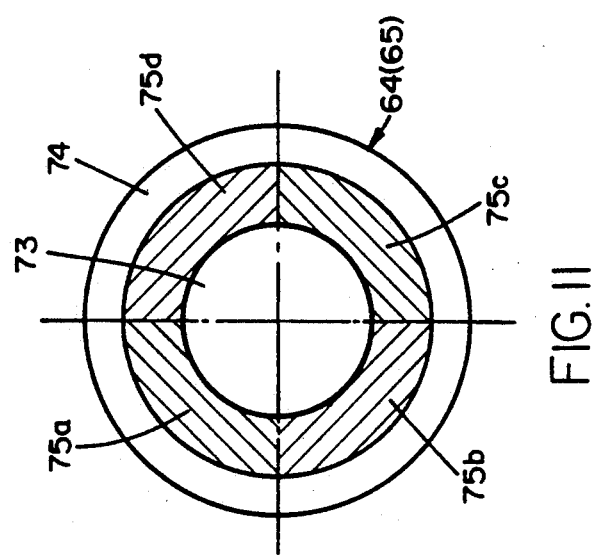
FIG. 11 is a view showing a filter.

FIG. 11 indicates the filter 64 (or 65). The filter 64 has a light-screening region 73 in the central portion and a light-screening region 74 in the peripheral portion. Numeral 75a–75d each indicate a light-transmitting region through which a light having a predetermined wavelength is transmitted. In this embodiment, the regions 75a and 75c allow a red-colored light flux to be transmitted, while the regions 75b and 75d allow a blue-colored light flux to be transmitted.

Referring to FIGS. 10 and 11, there will hereunder be explained a system for applying red- and blue-colored lights to the surface of the wafer 50 respectively from different directions.

Light (white-colored) irradiated from the light source 5 passes through the condensing lens to become a parallel light flux 71 which is then made incident on the filter 64. The lights transmitted through the regions 75a–75d of the filter 64 are turned to be sectionally ring-like light fluxes 76 and 77 in which the red lights and blue lights are alternately positioned in the respective quadrants as is shown in FIG. 11, and said light fluxes 76 and 77 pass to a half mirror 78 where they are reflected. These light fluxes so reflected are further reflected at the light path-changing mirrors 56 and 57 and reach the wafer 50. In this manner, lights (red and blue lights) respectively having different wavelengths are made incident on the wafer 50 from the respective different direction.

As mentioned above, only the lights made incident from the respective predetermined directions depending on the configuration of the etch pit are made incident on the object lens 53 as reflected lights. These reflected lights are transmitted through the half mirror 78 and via the condensing lens 63 to the image pickup surface 80 of the TV camera 6, thus obtaining image data by the TV camera 6. Since the TV camera 6 is a color camera, image data of the red-colored reflected light and that of the blue-colored reflected light can be separately obtained.

A filter is provided at a position designated at numeral 64 or 65 for dividing into spectra the lights to be made incident on the wafer in FIG. 10, but the same filter may be provided at a position designated at 81 instead.

The image data of the reflected lights obtained on the respective wavelengths is subjected to computation (addition) by the image processing unit 7 and the computer 8 thereby to enable all defects to be observed.

On the other hand, in cases where light is irradiated onto foreign matter such as dust on the surface of a wafer, the foreign matter will appear in images obtained from light irradiated from any direction. Thus, elimination of only foreign matter such as dust on the surface of the wafer from the image or lowering of image level of the foreign matter to such a level as is easily eliminable from the image can be carried out by obtaining exclusive-or (EX-OR) of the images obtained from illumination lights coming from the respective four directions.

Figure 12:
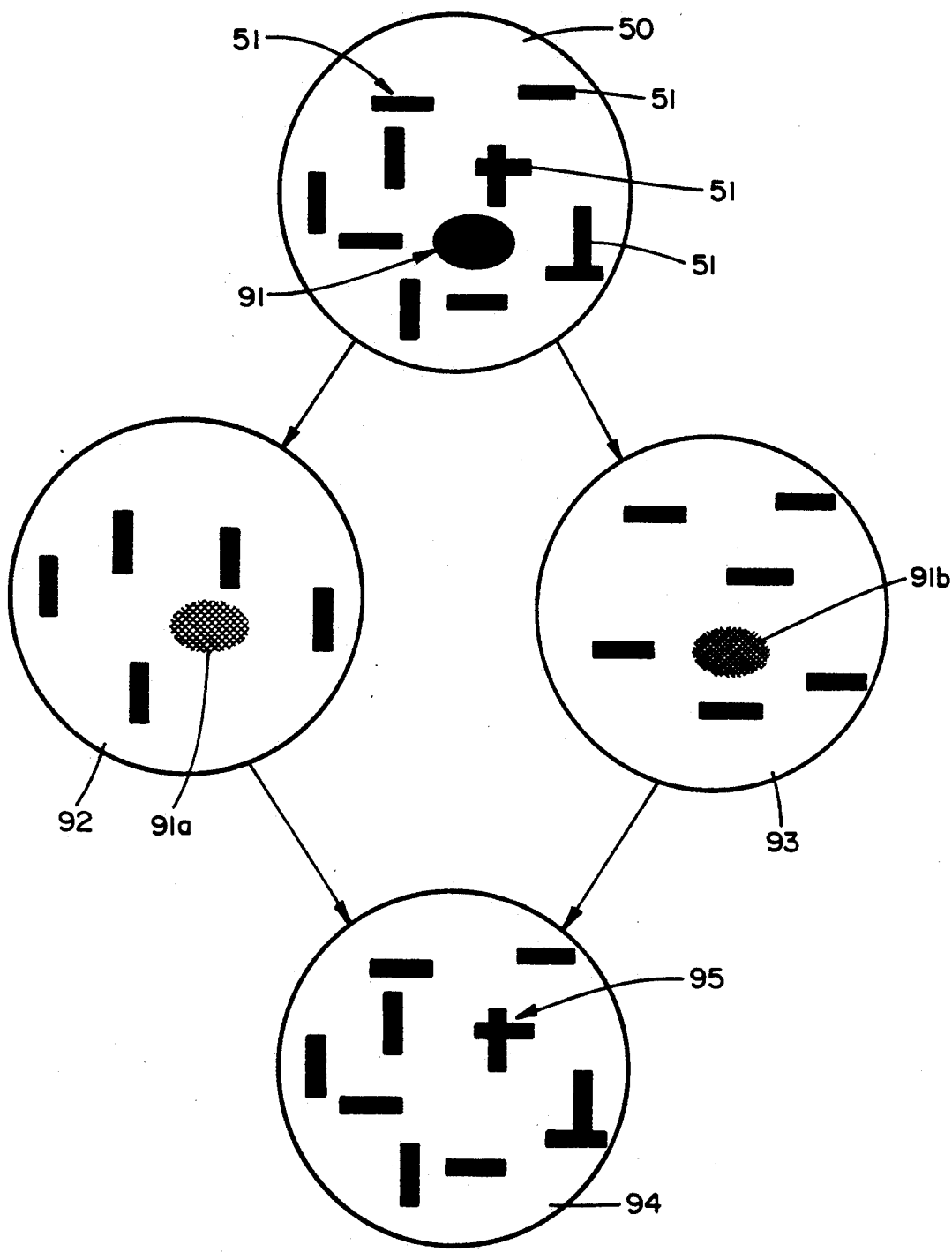
FIG. 12 is a conceptional view showing how foreign matters and flaws are eliminated by the image processing means.

FIG. 12 shows how image data obtained due to the foreign matter and flaws is eliminated by such image processing as above. Referring to this Fig., not only a plurality of etch pits 51 but also dust 91 are present on the surface of the wafer sample 50. Blue-colored light fluxes and red-colored light fluxes are made incident on the wafer sample 50 from directions in which these light fluxes are perpendicular to each other viewed from the plan view, thereby to obtain image data in the respective colors. Numeral 92 is image data obtained by the blue-colored light flux; and numeral 93, image data obtained by the red-colored light flux. The image data 92 includes etch pits extending in the longitudinal direction of the Figure, and the image 91a of dust 91. The image data 93 includes etch pits extending in the lateral direction of the Figure, and the image 91b of dust 91.

Numeral 94 indicates image data obtained by computation of exclusive-or (EX-OR) of the image data 92 and 93 of the respective colors. By computing EX-OR, the image data 91a and 91b of the dust is eliminated while leaving only the image data of the etch pits.

Figure 13:
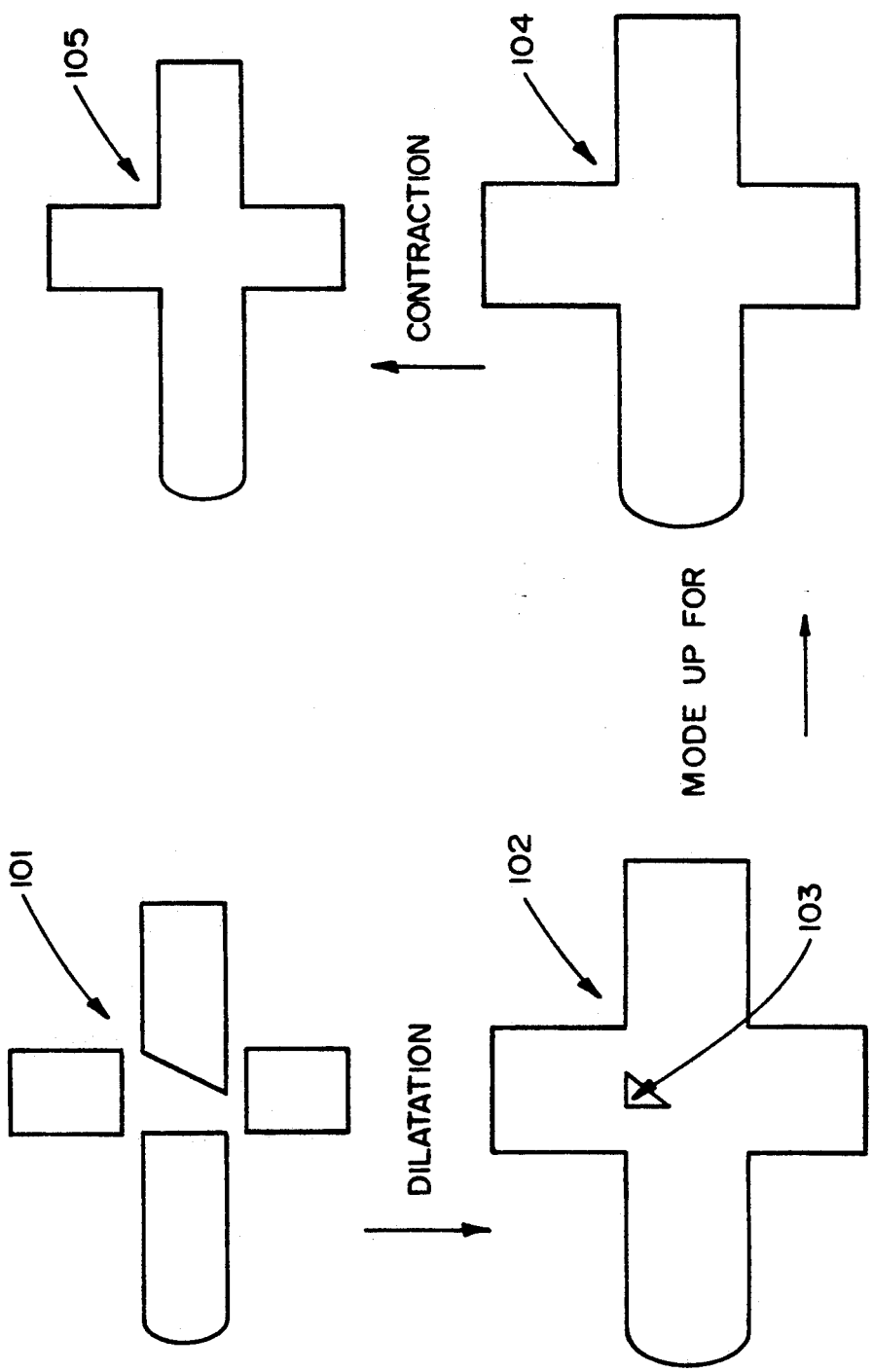
FIG. 13 is a conceptional view showing how to determine the overlapping of etch pits by dilating and contracting image data.

Further, two etch pits overlapping each other, designated at numeral 95 are eliminated simply by taking EX-OR and, thus, they are processed in a different way than dust and the like are processed. To achieve this for example, as indicated in FIG. 13, image data 101 is once dilated (or magnified) to reduce an overlapped region 103 in size as is seen from image data 102, and the thus reduced overlapped region then undergoes hole filling to give the image seen in 104. Thereafter, the image data 104 is contracted (thinned) to obtain appropriate image data 105. In addition, the overlap of etch pits can also be judged by calculating the peripheral length versus area of an image obtained.

FIG. 14 is a graph obtained by expressing peripheral length versus area in terms of circular image and rectangular image. Referring to this Figure, the abscissa indicates a peripheral length L and the ordinate indicates an area S. Numeral 111 is a graph of the peripheral length versus area of the circular image, and numeral 112 is a graph of the peripheral length versus area of the rectangular image. In cases where these images are separated from each other, if the result obtained by, for example, calculating the peripheral length and area of an image to be judged falls within a hatched region 113 then it is judged to be rectangular, while if not, then it is judged to be circular.

In general, etch pits formed due to oxidation induced stacking fault (OSF) vary in length, and if a histogram of length is measured to find a peripheral length of a certain level or higher than it can be judged that the pits overlap each other. In FIG. 14 for example, if average peripheral length is 35 μm then pits positioned at a point B are judged to be two pits overlapping each other.

Such processing as above can be realized at a high speed by using comparatively simple software in the computer 8 and the image processing unit 7.

FIGS. 15A-18B are each photograph showing the wafer's crystal structure measured by the above Example.

Figure 15B:
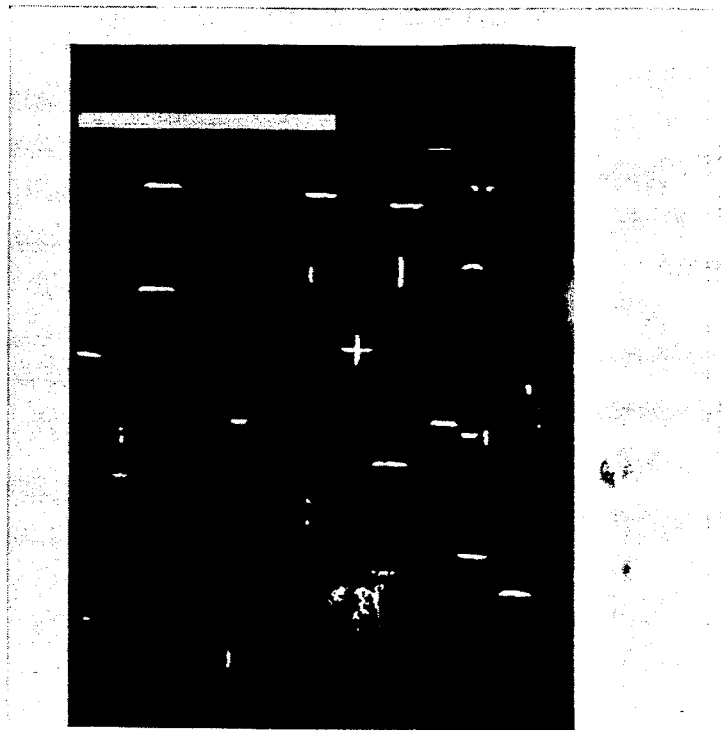
FIGS. 15A-18B are each photographs showing the crystalline structure of a wafer measured in the following Examples.
Figure 15A:
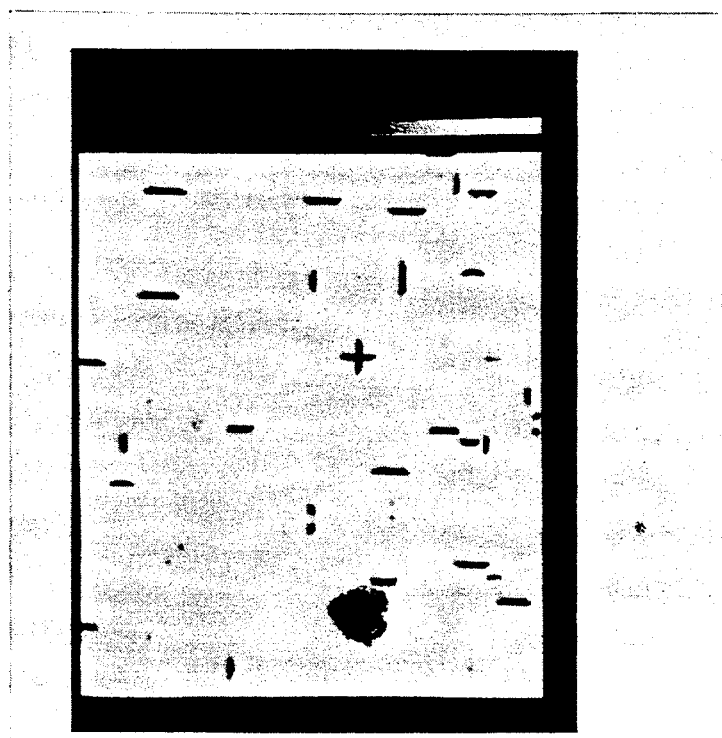

FIG. 15A is a photograph showing etch pits which are oxidation induced stacking faults on the wafer, and an ellipse present in the left side of this Figure is dust on the wafer. FIG. 15B indicates the binary image of FIG. 15A, and it is seen from FIG. 15B that the image of dust will remain as it is even if FIG. 15A is made binary.

Figure 16B:
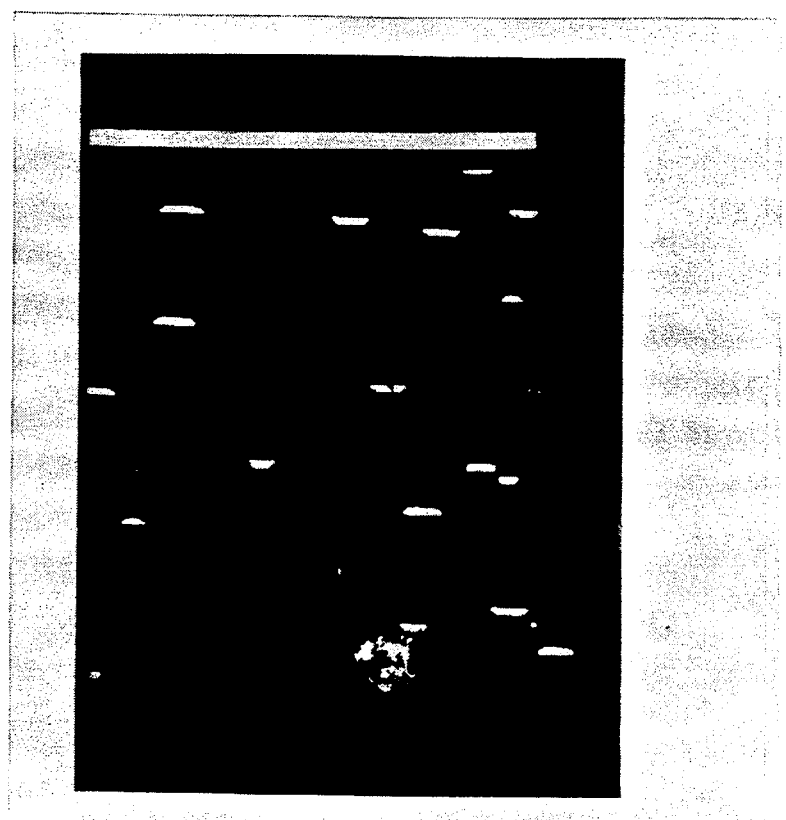
Figure 16A:
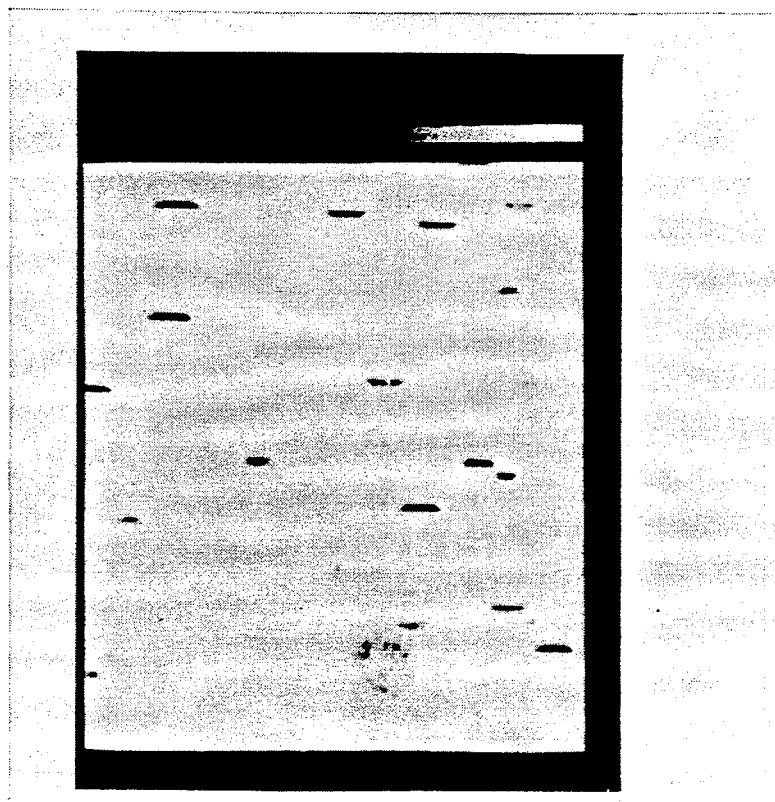
Figure 17B:
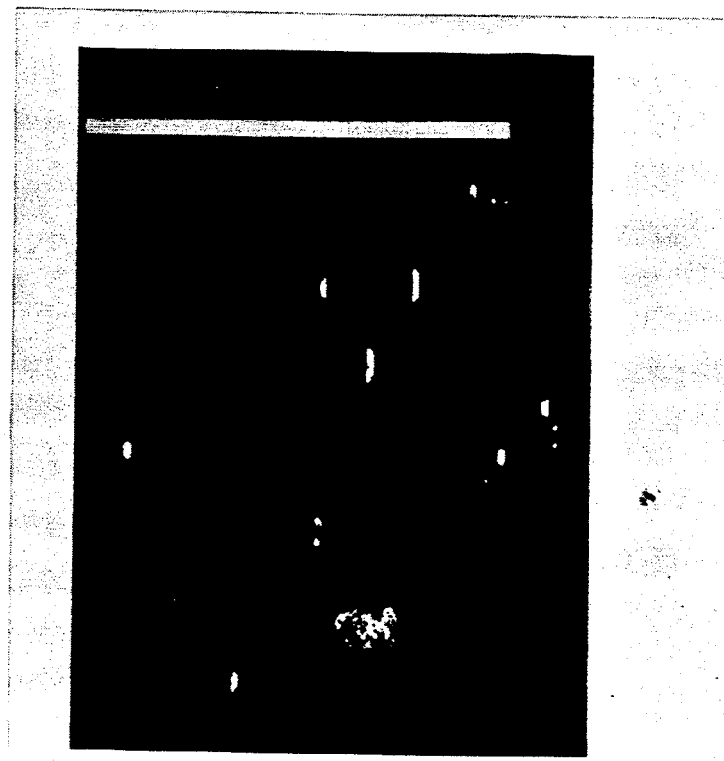
Figure 17A:
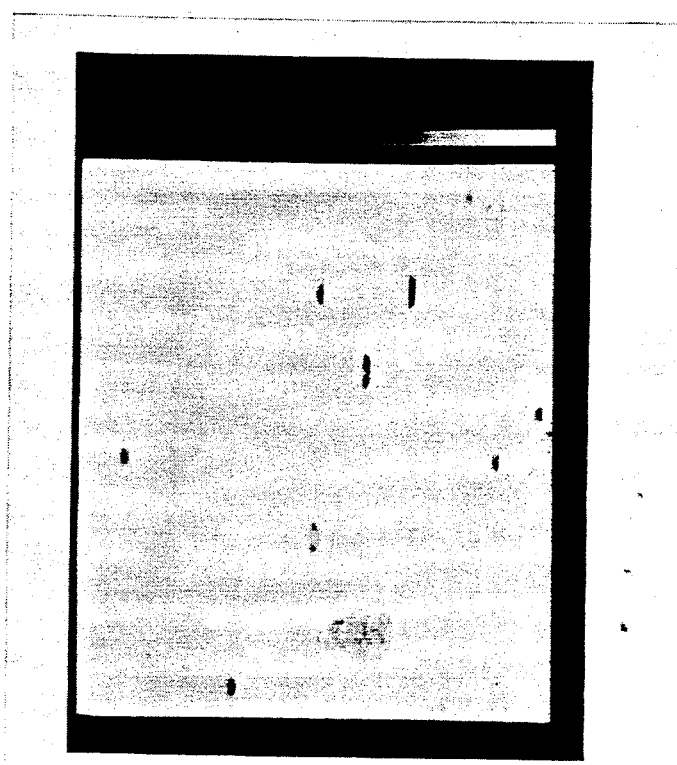

FIGS. 16A and FIG. 17A are photographs obtained by photographing the same place as in FIG. 15A by the apparatus of this invention while changing the light irradiation direction for every color of the light. The etch pits can be resolved into only those extending in the longitudinal direction or only those extending in the lateral direction. FIG. 16B and FIG. 17B are obtained by making FIG. 16A and FIG. 17A binary, respectively.

Figure 18B:
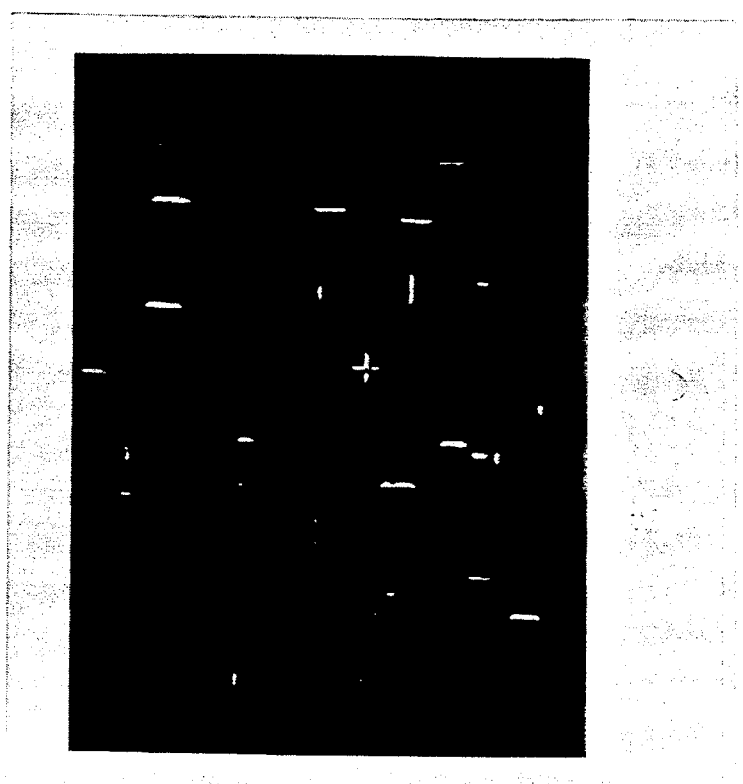
Figure 18A:
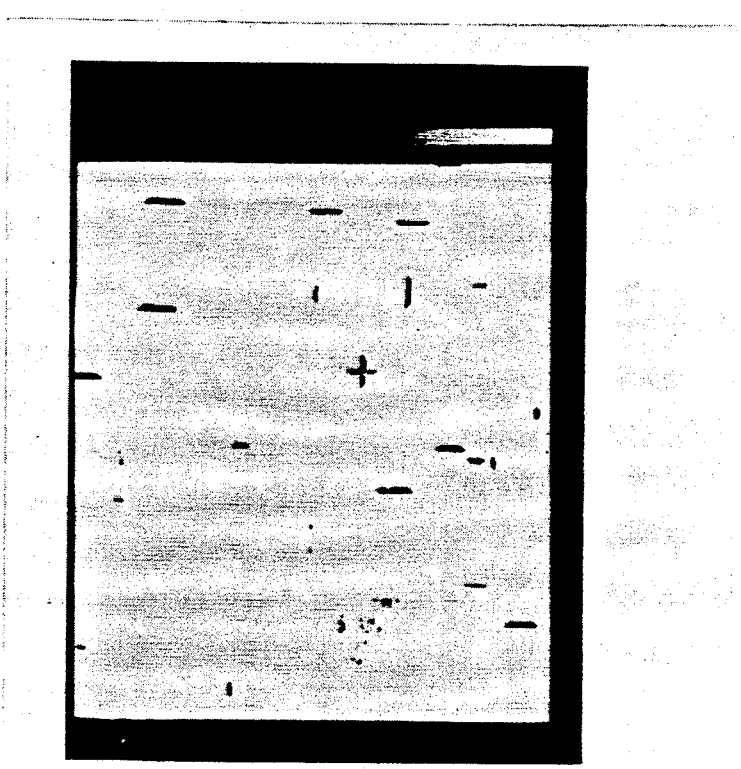

FIG. 18A and FIG. 18B indicate image data obtained by subjecting images of FIG. 16B and FIG. 17B to exclusive-or (EX-OR) computation, and a reversal image thereof, respectively. FIGS. 18A and 18B show that the image of dust has been almost eliminated or it has been so reduced as to be eliminable by image processing.

In the above embodiment (Example), two color illumination lights [for example, red light (R) and blue light (B)] which are easily separable by a color TV camera, are applied to crystal surfaces (51a, 51b and 51c, 51d in FIG. 5) to simultaneously obtain a R image and a B image which are then subjected to inter-image computation, thereby to eliminate the image of dust and then measure and estimate the crystal surface for crystal defects. The sample used in this Example was a silicon wafer, and two different color illumination lights were enough for the measurement and estimation since the number of crystal surfaces exposed were 4. Without being limited to this, in cases where, for example, six crystal surfaces are exposed as in GaAs, the kinds of illumination lights may be increased as required or other suitable means may also be available.

As to the light source used in this Example, a halogen lamp and filters were used; however, any light sources capable of irradiating a monochromatic light may be used.

The objects to be measured in the above Example were limited to crystalline materials (wafer), but objects to which this invention is applied are not limited to such objects as used in the above Example. In addition to crystalline materials, other materials such as non-crystalline materials (glass for example) and polycrystalline materials (ceramics for example) may also be measured and estimated for surface defects by the apparatus of this invention.

In the above second Example, a strobe light may be used as a light source under such control as mentioned in the first Example. That is, the first and second Examples may be combined together. Such a combination enables a material to be accurately measured and estimated for its surface defects at a very high speed without being influenced by dust and flaws.

As mentioned above, according to the apparatus, the image of a to-be-inspected object on the stage, is fetched under the lighting means flashed synchronously with the movement of the stage and, at the same time, the image data is fetched in the image processing means; thus, the object such as a crystal can be measured for its defects without rendering the stage stationary. Accordingly, the apparatus of this invention makes it possible to measure and estimate the object for its defects at a high speed thereby to remarkably enhance the apparatus itself in performances.

Further, according to this invention, a plurality of illumination lights having respective different wavelengths are irradiated to the object from respective predetermined different directions to obtain image data on the respective different wavelengths and then inspect the object for defects, and, therefore, even in cases where flaws and foreign matter such as dust are present on the surface of the object, this invention makes it possible to correctly and precisely distinguish etch pits from other items such as dust thereby to enable satisfactorily precise measurement and estimation to be achieved.

What is claimed is:

1. A surface inspecting apparatus for measuring and estimating etch pits of a sheet-like object to be inspected, comprising:

a movable stage with the object mounted thereon,
   a source of white light for lighting the surface of the object by making a plurality of illumination lights respectively having different wavelengths incident on the surface of said object from respective predetermined different directions,
   image pickup means for fetching the image of the object under illumination of said lighting means as image data obtained on the respective different wavelengths,
   means for moving said stage in the X-direction which is the longitudinal vertical direction, in the Y-direction which is the left and right side, in the Z-direction which is perpendicular to the plane of said stage and in the θ direction which is the direction of rotation around said Z-direction,
   image data processing means comprising a color camera for measuring and estimating said image data for etch pits of the object,
   means for reflecting the light of different wave length, and changing the light path and computer means for determining said etch pits by computation.

2. The surface inspecting apparatus according to claim 1 wherein said object has on its surface thereof dust and foreign matter, blue colored light fluxes and red colored light fluxes are incident on said object from directions perpendicular to each other when viewed from the plan view and said computer means are adjusted to subject said image data obtained on the respective different wavelengths to computation of exclusive-or (EX-OR); whereby the effect of dust and foreign matter is eliminated.

3. The apparatus according to claim 1 wherein said object to be inspected is a member selected from the group of crystalline materials, glass and ceramic.

4. A surface inspecting apparatus for measuring and estimating the surface of a sheet-like object to be inspected, comprising:
    a movable stage with a to-be-inspected object mounted thereon,
    a source of white light for lighting the surface of the object by making a plurality of illumination lights respectively having different wavelengths incident on the surface of the object from respective predetermined different directions,
    means for moving said stage in the X-direction which is the longitudinal vertical direction, in the Y-direction which is the left and right side, in the Z-direction which is perpendicular to the plane of said stage and in the $\theta$ direction which is the direction of rotation around said Z-direction,
    image pickup means for fetching the images of parts of the object as image data obtained on the respective different wavelengths,
    image processing means for measuring and estimating the image data obtained on the respective different wavelengths for etch pits of the object, and
    synchronization control means for flashing said lighting means and simultaneously fetching the image data obtained on the respective different wavelengths by said image pickup means, synchronously with the object mounted on the stage reaching respective predetermined positions while moving said stage.

5. The surface inspecting apparatus according to claim 4 wherein said object has on its surface thereof dust and foreign matter, blue colored light fluxes and red colored light fluxes are incident on said object from directions perpendicular to each other when viewed from the plane view and said computer means are adjusted to subject said image data obtained on the respective different wavelengths to computation of exclusive-or (EX-OR); whereby the effect of dust and foreign matter is eliminated.

6. The apparatus according to claim 4 wherein said object to be inspected is a member selected from the group of crystalline materials, glass and ceramic.

7. A surface inspecting apparatus for measuring and estimating the surface of a sheet-like object to be inspected, comprising:
    a movable stage with the object mounted thereon,
    a source of white light for lighting the surface of the object by making a plurality of illumination lights respectively having different wavelengths incident on the surface of the object from respective predetermined different directions.
    image pickup means for fetching the images of parts of the object as image data obtained on the respective different wavelengths,
    image processing means for measuring and estimating the image data obtained on the respective different wavelengths for etch pits of the object, and
    synchronization control means for flashing said lighting means and simultaneously fetching the image data obtained on the respective different wavelengths by said image pickup means, at a predetermined time interval starting at the time of commencement of movement of said stage.

8. The surface inspecting apparatus according to claim 7 wherein said object has on its surface thereof dust and foreign matter, blue colored light fluxes and red colored light fluxes are incident on said object from directions perpendicular to each other when viewed from the plane view and said computer means are adjusted to subject said image data obtained on the respective different wavelengths to computation of exclusive-or (EX-OR); whereby the effect of dust and foreign matter is eliminated.

9. The apparatus according to claim 7 wherein said object to be inspected is a member selected from the group of crystalline materials, glass and ceramic.

* * * * *